(12) United States Patent
Maslanka

(10) Patent No.: US 8,479,344 B2
(45) Date of Patent: Jul. 9, 2013

(54) CLEANING WICK FOR A CHANNEL OF A MEDICAL INSTRUMENT

(76) Inventor: Herbert Maslanka, Tuttlingen (DE)

( * ) Notice: Subject to any disclaimer, the term of this patent is extended or adjusted under 35 U.S.C. 154(b) by 825 days.

(21) Appl. No.: 12/448,990

(22) PCT Filed: Jan. 15, 2008

(86) PCT No.: PCT/EP2008/000284
§ 371 (c)(1),
(2), (4) Date: Jan. 25, 2010

(87) PCT Pub. No.: WO2008/087016
PCT Pub. Date: Jul. 24, 2008

(65) Prior Publication Data
US 2010/0139018 A1     Jun. 10, 2010

(30) Foreign Application Priority Data
Jan. 18, 2007   (DE) .................... 20 2007 000 793 U

(51) Int. Cl.
*B08B 9/04*   (2006.01)
(52) U.S. Cl.
USPC ..................................... 15/104.05; 15/104.16
(58) Field of Classification Search
USPC ............. 15/104.03, 104.05, 104.095, 104.16, 15/164, 211
See application file for complete search history.

(56) References Cited

U.S. PATENT DOCUMENTS

| 4,922,936 A | * | 5/1990 | Buzzi et al. ............... 132/321 |
| 5,297,310 A | | 3/1994 | Cox et al. |
| 6,857,157 B1 | * | 2/2005 | Hoyle ..................... 15/104.05 |
| 2003/0044752 A1 | * | 3/2003 | Fischer et al. ............. 433/102 |
| 2006/0162105 A1 | * | 7/2006 | Abe ......................... 15/104.2 |

FOREIGN PATENT DOCUMENTS

| DE | 20309295 U1 | | 9/2003 |
| DE | 10 2004 038 583 | * | 2/2006 |
| DE | 10 2006 001 076 | * | 7/2006 |
| JP | 2002051978 A | | 2/2002 |
| JP | 2004222889 A | | 8/2004 |

OTHER PUBLICATIONS

International Preliminary Report on Patentability dated Jul. 30, 2009.

* cited by examiner

*Primary Examiner* — Randall Chin
(74) *Attorney, Agent, or Firm* — Edwards Wildman Palmer LLP; Scott D. Wofsy

(57) ABSTRACT

Disclosed is a cleaning wick for a channel of a medical instrument, particularly an endoscope. Said cleaning wick supports at least one, preferably several wiping elements (9) on the elongate, flexible wick (1) that can be inserted into the instrument channel. The wiping elements (9) are designed as flock coating that adheres to the wick (1) in a section of the length thereof. Unflocked zones (11) that are left between the wiping elements (9) absorb substances which are to be discharged from the instrument channel during the cleaning process. An unflocked final region (13) located at the longitudinal ends (3, 5) of the wick (1) makes it easier to introduce the cleaning wick into the instrument channel.

22 Claims, 1 Drawing Sheet

CLEANING WICK FOR A CHANNEL OF A MEDICAL INSTRUMENT

The invention relates to a cleaning wick for an instrument channel of a medical instrument, in particular an endoscope or the like.

Instrument channels of reusable medical instruments, such as endoscopes or cannulas or catheters, as are also used, for example, in ear, nose and throat medicine, also have to be cleaned in the interior of the channel using a cleaning wick. Conventional cleaning wicks (U.S. Pat. No. 5,297,310) have an elongate, flexible, tubular support element supporting a brush at one longitudinal end, or usually at both longitudinal ends. The brush has a bristle support composed of two wire sections twisted against one another which clamp the bristles between them. The bristle support is inserted into the longitudinal end of the tubular carrier element or wick and fixed at said location. The production of such a cleaning wick is relatively complex.

Conventional cleaning wicks with brushes, the bristles of which are bound to a bristle support, tend to spray cleaning fluid or substances led out of the instrument channel and this can lead to a contamination of the surroundings with material, some of which is infectious. In order to prevent such spray contamination, DE 10 2006 001 076 A1 discloses letting the wick protrude above the brush so that the brush can already be carefully pulled out of the instrument channel without the entire brush at the same time also snapping to the side as a result of the inherent elasticity of the wick. However, the known cleaning wick cannot prevent the relatively long bristles, which in turn are elastic, from spraying cleaning fluid or the like when said bristles emerge from the instrument channel and snap open.

In order to also avoid contamination effects by the brush as such, JP 2002 051 978 A and JP 2004 222 889 A1 disclose placing a cap onto the mouth of the instrument channel, the cleaning wick and the brush attached thereto being pulled out of the instrument channel through said cap. Although the cap protects the surroundings from being contaminated, it does constitute a cost factor and makes handling of the cleaning wick more difficult.

DE 203 09 295 U1 discloses a dental hygiene rod which is flocked and/or foamed in the region of its outer end.

It is the object of the invention to provide a cleaning wick for an instrument channel of a medical instrument, which can be produced more easily and more cost-effectively than was previously possible so that it can also be used as a single-use disposable article and moreover it can be handled more easily during use than was previously possible. In particular, what is intended to be achieved is that the cleaning wick does not tend to spray.

The invention assumes a cleaning wick for an instrument channel of a medical instrument, in particular an endoscope or the like, comprising an elongate, flexible wick which can be inserted into the instrument channel and at least one wiping element which is held on the wick and protrudes resiliently over the circumference of the wick, and is characterized in that the wiping element is designed as flock coating adhering to a portion of the length of the wick. Surprisingly, it was found that such a simple cleaning wick, which can be produced very cost-effectively, can also satisfactorily clean very narrow instrument channels with, for example, an internal diameter of less than 3.2 mm, e.g. 0.6 mm to 2 mm, even if the instrument channels have a length of a number of meters. It is particularly advantageous for the bounce of the fibers of the flock coating to be so low that the wiping elements do not or hardly tend to spray when they are pulled out of the instrument channel again once the cleaning has been effected. Hence, a contamination of the surroundings by cleaning fluid and the like being sprayed does not have to be feared.

A wick is generally intended to be understood to be an elongate, thin, flexible carrier element, for example a string, a tube, a wire or a strand, or the like. The wick is preferably composed of plastic, but can also be composed of metal or textile material.

Unlike conventional, brush-shaped cleaning wicks in which comparatively thick and hence rigid bristles protrude evenly in the radial direction, the fibers of cleaning wicks according to the invention have a more or less random orientation, as resulting from the flocking process. The fibers have a comparatively small diameter and hence are flexible, despite their comparatively short length. Cleaning wicks according to the invention "wipe" the secretion to be removed from the instrument channel in a gentle manner, while conventional, brush-shaped cleaning wicks are more likely to "scratch off" the secretion from the interior of the instrument channel. It is essential that the fiber density in flocked wiping elements is significantly higher than in the case of conventional brushes with bristles held using a brush-binding technique. Moreover, flocked fibers are distributed evenly over the flock coating region, which is not the case in conventional brushes. As a result of the higher fiber density and the even areal distribution, flocked wiping elements absorb fluid secretions better than conventional brushes produced using a brush-binding technique.

The fibers of the flock coating regions preferably have a diameter of less than 0.1 mm, in particular of less than 0.06 mm. Fibers with a diameter of less than 0.035 mm were found to be particularly expedient. Such fibers are flexible and only have a relatively small restoring force so that they gently glide over the inner face of the instrument channel and do not tend to spray when the wiping element is pulled out of the instrument channel. Fibers with such a small diameter can be cut to form staple fibers, the fiber ends of which have edges which are less sharp than is the case in conventional bristles of cleaning brushes. This also reduces the abrasion of the instrument channel during cleaning compared to conventional cleaning brushes.

The flock coating region of the wiping element can surround the wick in an annular fashion so that the instrument channel is cleaned evenly over its entire circumference. However, provision can also be made for the flock coating region of the wiping element to surround the wick in a helical fashion with at least one winding. Additionally, in the case of a helical design of the flock coating region, flock-coating-free regions remain between the coil sections, in which regions the substances to be removed by the cleaning process can be collected. The last-mentioned advantageous object can also be achieved in the case of annular flock coating regions which surround the wick if the wick in at least one portion of its length supports a group of a number of wiping elements arranged at a distance from one another along the length of the wick.

In a preferred refinement, the wiping element or a number of the wiping elements are arranged in the region of at least one of the longitudinal ends, preferably in the region of both of the longitudinal ends, of the wick. If the wick supports wiping elements only in the region of one of its longitudinal ends and if said wick is long enough, the wick can be completely pushed through the instrument channel so that the wiping element on the wick can be pulled through the instrument channel. If the wick supports wiping elements at both ends, the cleaning wick must indeed be pushed through the instrument channel; however, in this case, care does not have to be taken during handling as to which end is in front as the wick is inserted into the instrument channel.

Expediently, the at least one wiping element is arranged at a distance from the longitudinal end of the wick. The advantage of this is that the longitudinal end can more easily be inserted into the instrument channel.

In order to prevent damage to the instrument channel, at least one of the longitudinal ends, preferably both longitudinal ends, of the wick is or are chamfered. The chamfering can also be formed by a chamfered bulge, for example a spherical bulge. In one variant, in which the wiping element adjacent to the longitudinal end of the wick immediately adjoins the longitudinal end of the wick, this wiping element can extend over both the circumference of the wick and the end face thereof. This too can counteract damaging the instrument channel.

Instrument channels of cannulas or the like, as are used in ear, nose and throat medicine, often have an internal diameter of 1 mm or less. In a refinement suitable for such narrow instrument channels, provision is made for the wiping element or a number of the wiping elements to be arranged in a central portion of the wick and at a distance from the two longitudinal ends thereof, the distance of the at least one wiping element from the longitudinal ends expediently being greater than the length of the instrument channel to be cleaned. The wiping element can be pulled through the instrument channel independently of which longitudinal end is in front as the cleaning wick is inserted into the instrument channel. However, a pushing operation is often not possible in such cleaning wicks as a result of the very small wick diameter.

Although the wick can also be of tubular design, a wick with a solid cross section is preferred due to its improved stiffness against kinks. The wick can be composed of plastics or metal. In particular for the use in very narrow instrument channels with, for example, a diameter of less than 1 mm, the wick is preferably composed of a memory metal.

The flock coating is preferably composed of short fiber sections which mainly protrude radially from the wick when they are applied electrostatically. The high density of the fiber sections improves the cleaning effect. It is goes without saying that the flock coating can also be applied differently, for example using a printing process or an immersion process or a top-blowing process, in which the wick, coated with an adhesive or the like at the locations of the wiping elements, is immersed into a fiber store, or the fibers are blown onto the wick.

The fibers are preferably composed of plastic material, preferably polyamide, but also polyester or viscose or the like. However, the fibers can also be natural fibers, e.g. cotton fibers. Natural fibers are advantageous in that they can absorb liquids more easily. Depending on the application, the fibers can have a smooth surface which assists the wiping effect. In the case of a rough surface, the abrasive effect is assisted so that even dried-on substances can be removed from the instrument channel.

The diameter and the length of the fibers influence the cleaning properties. The longer and thinner the fibers are, the more softly and gently the instrument channel is cleaned. Thick, short fibers assist the abrasive effect. The larger the diameter of the instrument channel is, the larger the diameter and length of the fibers should be. It goes without saying that the wiping elements can be flocked by mixtures of fibers of different material and/or diameter and/or length. It is also possible for wiping elements following one another to be composed of fibers of different material, different diameter or different length, so that wiping elements following one another on the wick have different cleaning effects, for example such that the abrasive effect of wiping elements or wiping element groups following one another decreases or increases in a staged fashion.

In a further refinement, a brush with bristles radially fixed to a bristle support can be attached to at least one of the longitudinal ends of the wick in addition to a wiping element, formed by a flock coating, provided in the region of the longitudinal end, or else at a distance therefrom, for example between the longitudinal ends. The brush can be a conventional brush with a bristle support composed of two wire sections twisted against one another which clamp the bristles between them. Expediently, the wick is designed as a tube in such a refinement so that the bristle support can be inserted into the longitudinal end of the tube and be fixed at said location.

In the following text, exemplary embodiments of the invention are explained in more detail using a drawing, in which.

Figure 1:
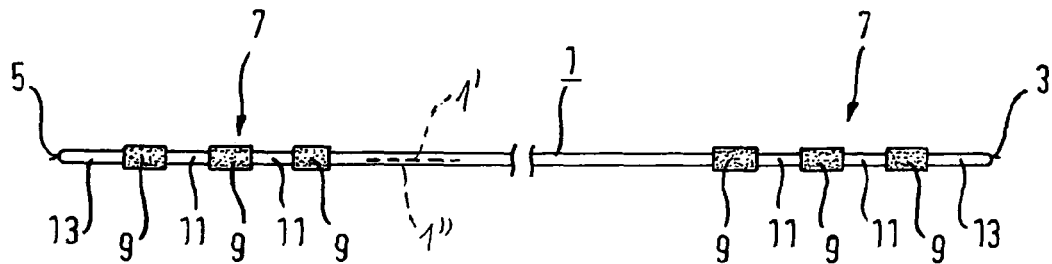
FIG. 1 shows a cleaning wick for cleaning an endoscope channel.

The cleaning wick for cleaning a long, narrow endoscope channel illustrated in FIG. 1 has an elongate wick 1 in the form of an elongate support element of flexible plastic material with a solid cross section, the diameter of which wick is less than the internal diameter of the instrument channel to be cleaned. In the region of its two longitudinal ends 3, 5, the outer shell of the wick 1 is provided in each case with a group 7 of a number of, in this case three, wiping elements 9 which are respectively arranged at a distance from one another by a wiping element free region 11 and arranged at a distance from the longitudinal ends 3 and 5 by a wiping element free region 13. It goes without saying that the wiping element free region 13 can also possibly be dispensed with. Each of the wiping elements 9 is designed as a resilient flock coating adhering to a portion of the length of the wick 1. The flock coating protrudes over the external circumference of the wick 1 so that the external diameter of the wiping elements 9 is slightly larger than the internal diameter of the instrument channel to be cleaned. The flock coating is preferably composed of elastic plastic short fibers which have preferably been applied to the wick 1 electrostatically. Unlike conventional brushes bound from individual bristles, wiping elements 9 formed by flocking do not tend to spray when being pulled out of the instrument channel.

The wick 1 can be designed as a tube, but can also be solid. In a preferred refinement, the wick 1 has a core 1' in the form of a metal wire coil or wire strand which is coated by a plastic shell 1" supporting the flock coating. Such a wick combines high kink-stiffness with sufficiently high flexibility. The plastic shell 1" can be flocked to the core 1' with a permanent adhesive, while the metal core 1' is resistant to breaking to a high degree and correspondingly wick breakage in the instrument channel does not have to be feared.

The wick 1 is longer than the instrument channel to be cleaned, the latter for example being 1 to 3 m long in the case of medical endoscopes. The diameter of the wiping elements 9 is slightly larger than the internal diameter of the instrument channel which is approximately 2 to 3.2 mm in the case of medical endoscopes. In ear, nose and throat medicine, in laparoscopy and in urology, wick lengths of up to approximately 1 m suffice, with it also being possible for the channel internal diameter to be greater than 3 mm in laparoscopy and less than 2 mm in ear, nose and throat applications. The diameter of the fibers is expediently less than 0.1 mm and preferably less than 0.06 mm. Fibers with a diameter of less than 0.035 mm are particularly advantageous. The fibers are applied to the flock coating regions with a basically random orientation and, to be precise, substantially evenly over the area of the flock coating region. This makes it possible for the flock coating region to absorb liquid secretions particularly well and guide them out of the instrument channel.

The external diameter of the wiping elements 9 has to be slightly larger than the internal diameter of the instrument channel. The excess depends on the flock coating density, the external diameter of the wiping elements 9 and the length of the flock coating fibers.

The regions without flock coating 11 between the wiping elements 9 form collection spaces for substances to be removed from the instrument channel. The region without flock coating 13 simplifies the insertion of the cleaning wick into the instrument channel. Since wiping elements 9 are arranged in the region of both longitudinal ends 3, 5, each of the two longitudinal ends 3, 5 can be inserted first into the instrument channel without having to worry about the alignment. The longitudinal ends 3, 5 are expediently chamfered to avoid damage to the instrument channel. It goes without saying that wiping elements 9 can be provided at only one of the longitudinal ends.

In order to limit the push-resistance during the insertion of the cleaning wick into the instrument channel, 3 to 4 wiping elements 9 per group 7 were found to be expedient. The number of wiping elements should be selected such that the frictional force resulting during operation does not lead to a kink in the wick 1. The length of the wiping elements 9 which surround the wick 1 in an annular fashion is expediently between 0.5 and 5 cm, preferably about 1 cm, while the length of the regions 11 is expediently selected to have the same order of magnitude, i.e. between 0.5 and 1.5 cm, preferably about 1 cm. The overall length of the wiping elements is selected in accordance with the desired cleaning result; the longer the wiping elements are, the fewer wiping elements are provided. The plastic material of the wick 1 is selected such that it can absorb the pushing pressure exerted during the cleaning of the instrument channel without kinking. In one variant, wiping elements 9 with a length from 3 to 7 cm, in particular approximately 4 cm, were found to be expedient, especially when the distances between them, i.e. the regions 11, are longer and have a length of, for example, 5 to 9 cm, preferably approximately 7 cm.

The fibers of the wiping elements 9 are composed of polyamide, but can also be composed of polyester, viscose or other plastics. Natural fibers, such as cotton fibers, are also suitable. The fibers have a length of, for example, 0.5 mm to 1 mm and have a diameter of, for example, 0.1 mm to 0.15 mm. The thicker and shorter the fibers are, the harder the flock coating is and the more abrasive the cleaning effect is. Longer, thinner fibers assist the wiping effect. Differently abrasive properties can also be achieved by the surface structure of the fibers. The surface can be smooth or else it can be rough.

The wiping elements 9 can be flocked by uniform fibers; however, the flock coating can also consist of a mixture of fibers of different material and/or different thickness and/or different length and/or different surface structure in order to be able to match the wiping elements 9 to the cleaning function in an improved manner. For this purpose, the wiping elements 9 within each group 7 can also have uniform flocking, but the flock coating can vary from group to group in a staged fashion so that the abrasive effect decreases or increases in stages between groups which follow one another. It goes without saying that the cleaning property, for example the abrasive property of the wiping elements 9 following one another in the group, can also be staged.

In the following text, variants of the cleaning wick are explained. Components with the same effect are referred to using the reference numerals from FIG. 1 and provided with a letter so that they can be distinguished. The preceding description is referred to in each case for the explanation of the design and mode of action, and for possible variants.

Figure 2:
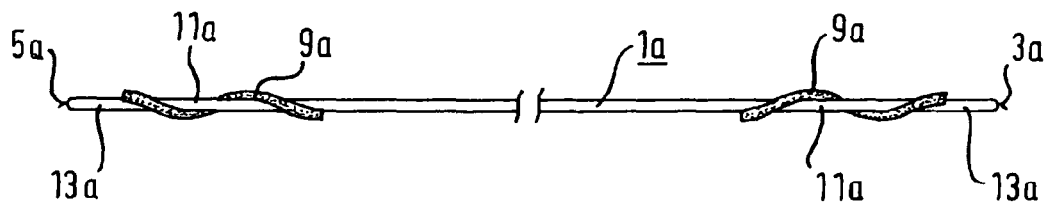
FIG. 2 shows a variant of the cleaning wick.

FIG. 2 shows a cleaning wick for the instrument channel of an endoscope or the like, with a wick 1a, produced from flexible plastic with a solid cross section or metal wire, which in the region of its chamfered longitudinal ends 3a, 5a in each case supports a wiping element 9a which loops around the external circumference of the wick 1a in a helical fashion over at least one winding. The wiping elements 9a in turn are composed of a short-fiber flock coating of the type explained above which protrudes over the circumference of the wick 1a. Regions 11a without flock coating, for holding the substances to be removed from the instrument channel when the latter is cleaned, remain between opposing winding sections. The wiping elements 9a are also arranged at a distance 13a, which is without flock coating, from the longitudinal ends 3a, 5a in order to ease the insertion of the cleaning wick into the instrument channel.

Figure 3:
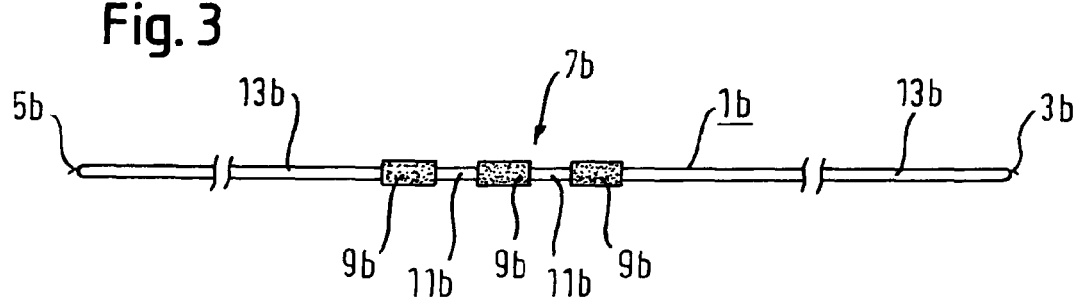
FIG. 3 shows a further cleaning wick provided in particular to clean short, narrow instrument channels in instruments from ear, nose and throat medicine.

In the embodiments of FIGS. 1 and 2, the wick 1 is so stable against kinking that the cleaning wick can be pushed into the cleaning channel with one of its longitudinal ends in front. FIG. 3 shows a variant of a cleaning wick which can also be used in very narrow instrument channels, as are used, for example, in medical instruments from ear, nose and throat medicine.

Instrument channels of this type often have an internal diameter of less than 1 mm, with the result that cleaning wicks which are suitable for said application tend to kink in the case of loading by pushing due to their small diameter. It is for this reason that the cleaning wick illustrated in FIG. 3 is designed so that it can be pulled through the instrument channel.

The cleaning wick has a wick 1b which supports a group 7b of a number of wiping elements 9b in the region between its two, possibly chamfered, longitudinal ends 3b, 5b. The wiping elements 9b surround the wick 1b in an annular fashion and are again arranged at a distance from one another whilst forming intermediate spaces 11b without a flock coating. Each of the wiping elements 9b is designed as a flock coated region. The wick 1b does not have a flock coating between the group 7b of the wiping elements 9b on the one hand and each of the two longitudinal ends 3b or 5b on the other hand. The length of this region 13b without flock coating is dimensioned to be larger than the length of the instrument channel so that the wick 1b can be completely pushed through the instrument channel before the closest wiping element 9b enters the channel. Hence, the wiping elements 9b can be pulled through the channel from the opposite end of the instrument channel. Since the cleaning wick substantially has a longitudinally-symmetric design, care does not have to be taken during handling as to which of its ends is inserted into the instrument channel.

Figure 4:
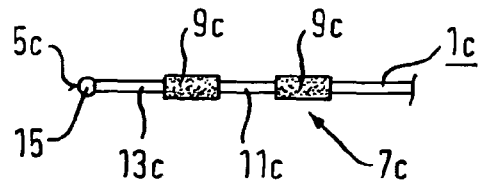
FIGS. 4 and 5 show further variants of the cleaning wick.

In the previously described exemplary embodiments, the longitudinal ends of the wire are chamfered to avoid damage to the instrument channel during the insertion of the wick. FIG. 4 shows a variant in which a chamfered bulge 15, e.g. a spherical bulge, is arranged on the longitudinal end, in this case the longitudinal end 5c of the wick 1c. The bulge 15 can be provided in each of the previously described exemplary embodiments.

Figure 5:
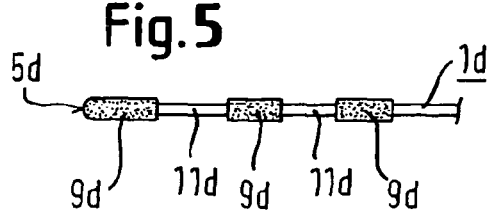

FIG. 5 shows a further variant of a cleaning wick, in which, at least one of the longitudinal ends, here the longitudinal end 5d, the wiping element 9d closest thereto extends not only over the circumference of the wick 1d, but also over the end face thereof forming the longitudinal end 5d. As a result of the end face of the wick 1d also being flock coated in this fashion, damage to the instrument channel can also be prevented.

Figure 6:
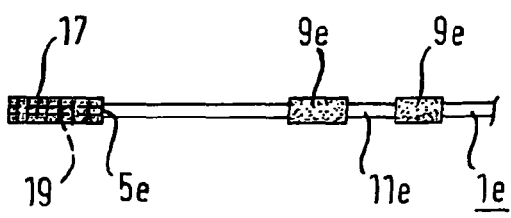
FIG. 6 shows a further variant of the cleaning wick with an additional brush.

In the previously explained exemplary embodiments, the cleaning wick only supports wiping elements formed by flock coating. FIG. 6 shows a variant in which at least one end face, here the end face 5e of wick 1e, holds a brush 17 with a bristle support 19, for a multiplicity of bristles attached radially to the bristle support 19, which is fixed to the wick 1e. The bristle support 19 can be a twisted pair of wires which clamp the bristles between them. The wick 1e is preferably a tube into which the bristle support 19 is inserted and fixed at said location. It goes without saying that bristles of the explained type can be provided at both longitudinal ends of the wick 1e. Between the two longitudinal ends, the wick 1e can be flock coated with a wiping element 9e or a number of such wiping elements 9e, as was explained above with reference to FIGS. 1 to 3. The wiping elements 9e can be provided individually or in groups in the region of the two longitudinal ends, or else they can be provided between the two longitudinal ends, for example towards the center.

The invention claimed is:

1. A cleaning device for an instrument channel of a medical instrument, the cleaning device comprising an elongate, flexible wick adapted to be inserted into the instrument channel and at least one group of wiping elements which are held on the wick at a distance from one another along the length of the wick and protrude resiliently over the circumference of the wick,
   wherein each wiping element is designed includes a flock coating adhering to a portion of the length of the wick, and
   wherein the wick has a metal wire core in the form of a metal wire strand which is coated by a plastic shell radially within the flock coatings and supporting the flock coatings.

2. The cleaning device as claimed in claim 1, wherein the flock coating of the wiping element surrounds the wick in an annular fashion.

3. The cleaning device as claimed in claim 1, wherein the flock coating region of the wiping element surrounds the wick in a helical fashion with at least one winding.

4. The cleaning device as claimed in claim 1, wherein the one group of the wiping elements is arranged in the region of a longitudinal end of the wick.

5. The cleaning device as claimed in claim 4, wherein wiping elements are arranged at a distance from the longitudinal end of the wick.

6. The cleaning device as claimed in claim 5 wherein the distance of the at least one wiping element from the longitudinal end is greater than the length of the instrument channel to be cleaned.

7. The cleaning device as claimed in claim 1, wherein groups of wiping elements are arranged in the region of both longitudinal ends of the wick.

8. The cleaning device as claimed in claim 1, wherein the wiping element or a number of the wiping elements are arranged in a central portion of the wick and at a distance from the two longitudinal ends thereof.

9. The cleaning device as claimed in claim 1, wherein the wick supports a number of wiping elements, the abrasive properties of which increase or decrease in a staged fashion along the wick.

10. The cleaning device as claimed in claim 9 wherein the wick supports a plurality of groups of wiping elements following one another along the wick, the abrasive properties of the wiping elements being staged from group to group.

11. The cleaning device as claimed in claim 9, wherein the abrasive properties of the wiping elements of said group are staged within the group.

12. The cleaning device as claimed in claim 1, wherein the wick supports a plurality of wiping elements, the flock coating of which is formed by fibers of different material and/or different diameter and/or different length and/or different surface roughness.

13. The cleaning device as claimed in claim 1, wherein the wick has a solid cross section.

14. The cleaning device as claimed in claim 1, wherein the flock coating consists of electrostatically applied, short fibers.

15. The cleaning device as claimed in claim 1, wherein at least one of the longitudinal ends of the wick is chamfered.

16. The cleaning device as claimed in claim 15, wherein at least one of the longitudinal ends of the wick is provided with a chamfered bulge.

17. The cleaning device as claimed in claim 1, wherein a wiping element is provided on at least one longitudinal end of the wick, the flock coating of which extends over both the circumference of the wick and the end face thereof.

18. The cleaning device as claimed in claim 1, wherein at least one of the longitudinal ends of the wick supports a brush with bristles fixed radially onto a bristle support and at least one wiping element, formed by flock coating adhering to the wick, is arranged between the longitudinal ends of the wick.

19. The cleaning device as claimed in claim 1, wherein the fibers of the flock coating have a diameter of less than 0.1 mm.

20. The cleaning device as claimed in claim 19, wherein the diameter of the fibers is less than 0.035 mm.

21. The cleaning device as claimed in claim 1, wherein the fibers of the flock coating have a basically random orientation relative to the wick.

22. The cleaning device as claimed in claim 1, wherein the fibers are composed of polyamide or viscose material.

* * * * *